United States Patent [19]

Green et al.

[11] 4,418,054

[45] Nov. 29, 1983

[54] POLYMERIC QUATERNARY AMMONIUM COMPOUNDS FOR SKIN CARE

[75] Inventors: Harold A. Green, Havertown, Pa.; John J. Merianos, Middletown; Alfonso N. Petrocci, Glen Rock, both of N.J.

[73] Assignee: Millmaster Onyx Group, Inc., New York, N.Y.

[21] Appl. No.: 348,827

[22] Filed: Feb. 16, 1982

Related U.S. Application Data

[63] Continuation-in-part of Ser. No. 119,948, Feb. 2, 1980, Pat. No. 4,325,940, which is a continuation-in-part of Ser. No. 29,778, Feb. 13, 1979, Pat. No. 4,304,910, which is a continuation-in-part of Ser. No. 980, Jan. 4, 1979, Pat. No. 4,188,293, which is a continuation-in-part of Ser. No. 902,894, May 4, 1978, Pat. No. 4,190,644, which is a continuation-in-part of Ser. No. 744,617, Nov. 24, 1976, Pat. No. 4,089,977.

[51] Int. Cl.$^3$ .................... A61K 31/785; A61K 7/48

[52] U.S. Cl. .......................................... 424/70; 424/78
[58] Field of Search ................................... 424/70, 78

[56] References Cited

U.S. PATENT DOCUMENTS

| | | | |
|---|---|---|---|
| 3,874,870 | 4/1975 | Green et al. | 424/329 |
| 4,029,817 | 6/1977 | Blanco | 424/81 |
| 4,038,995 | 8/1977 | Edelberg | 424/70 |
| 4,155,994 | 5/1979 | Merianos | 424/70 |
| 4,157,388 | 6/1979 | Christiansen | 424/70 |
| 4,381,919 | 5/1983 | Jacquet | 424/70 |
| 4,390,522 | 6/1983 | Jacquet | 424/70 |

*Primary Examiner*—Mark L. Berch
*Attorney, Agent, or Firm*—Arthur A. Jacobs

[57] ABSTRACT

A skin care additive for cosmetic compositions comprising uncapped linear polyquaternary ammonium compounds, the term "uncapped" being used to define those molecules whose termini are capable of further chain propogation.

2 Claims, No Drawings

POLYMERIC QUATERNARY AMMONIUM COMPOUNDS FOR SKIN CARE

This application is a continuation-in-part of application Ser. No. 119,948, filed Feb. 2, 1980 now U.S. Pat. No. 4,325,940, which is a continuation-in-part of application Ser. No. 29,778, filed Feb. 13, 1979 and now issued as U.S. Pat. No. 4,304,910 dated Dec. 8, 1981, which, in turn, is a continuation-in-part of application Ser. No. 980, filed Jan. 4, 1979 and now issued as U.S. Pat. No. 4,188,293 dated Feb. 13, 1980, this being a continuation-in-part of application Ser. No. 902,894, filed May 4, 1978 and now issued as U.S. Pat. No. 4,190,644 dated Feb. 26, 1980, the latter being a continuation-in-part of application Ser. No. 744,617, filed Nov. 24, 1976 and now issued as U.S. Pat. No. 4,089,977 dated May 16, 1978.

All of the disclosures of the above mentioned applications and patents are incorporated herein by reference.

In accordance with the present invention, compounds of the general formula:

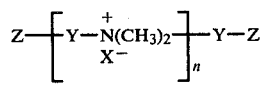

Formula (1)

wherein Z is X or $N(CH_3)_2$, Y is $-CH_2CHOH-CH_2-$ or $-CH_2CH=CH_2CH_2-$ and X is a halogen having an atomic weight above 30, and n is an integer from 2 to about 30, have been found to be excellent skin care products which, when used as an additive in standard skin care formulations, significantly increase the softness of the skin as compared to when the same formulations are used without such additive.

The above-identified preceding applications and patents disclosed the synthesis and uses of certain linear polymeric compounds made by reacting 1,3-dichloro-2-propanol with certain 1,3-bis-amino-2-propanols. These were referred to as polyquaternary ammonium compounds because their molecules were linear and contained quaternary ammonium groups as part of the polymeric linear chain. The general formula for this type of compound is:

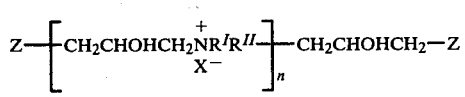

Formula (2)

where $R^I$ and $R^{II}$ are, inter alia, alkyl groups, X is a halogen whose atomic weight exceeds 30, n is an integer of from 2 to 20 and Z is either X or $NR^IR^{II}$.

It has now been discovered that compounds of the above chemical structure, but where n is an integer of from 2 to about 30, provide increased softness to the skin when used as an additive in standard skin care formulations, especially when $R^I=R^{II}=CH_3$.

The molecular representation of such compounds is as follows:

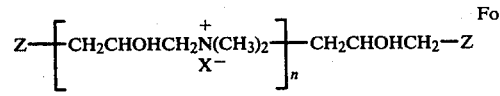

Formula (3)

where X and Z are the same as in Formula (2) and n is an integer of 2 to about 30.

When the above type compounds, are incorporated into cosmetic compositions utilized as skin creams, skin lotions, soap solutions, etc. they significantly improve the skincare properties, and particularly, the "feel" thereof. Although applicants have no intent to be bound by any theories, it appears that these uncapped polyquaternary compounds not only promote the deposition of a protective film on the skin but also improve the lubricity of such a film.

The following examples illustrate standard types of cosmetic formulations. These are stock skin care formulations, and, by themselves, do not form any part of the present invention since each formulation either duplicates a common formulation or is so very similar to such formulation that it might be considered "common".

EXAMPLE 1

| Moisturizing Lotion: | |
|---|---|
| Component | Percent by Wt. |
| "Arlacel 165" | 5.0 |
| Corn Oil | 2.0 |
| "Miglycol 840 Gel" | 3.0 |
| "Ammonyx 4002" | 1.0 |
| "BTC 2125M", 50% | 0.1 |
| "Natrasol 250 HHR" 3% aqueous | 10.0 |
| Distilled Water    q.s. | 100.0 |

"Arlacel 165" is a product of ICI Industries, Wilmington, Del., "Miglycol 840 Gel" is a product of Dynamit Nobel, Montvale, N.J., "Ammonyx 4002" and "BTC 2125M" are products of the Onyx Chemical Company, Jersey City, N.J., and "Natrasol 250 HHR" is a product of Hercules Inc., Wilmington, Del.

EXAMPLE 2

| Liquid Soap: | |
|---|---|
| Components | Percent by Wt. |
| "Maprofix WAC-LA" | 30.0 |
| "Onyxol 345" | 5.0 |
| Ethylene glycol monostearate | 2.0 |
| Sodium chloride | 1.5 |
| "Nimlesterol D" | 0.5 |
| "Permakleer 100" | 0.5 |
| Distilled Water    q.s. | 100.0 |

"Maprofix WAC-LA", Onyxol 345" and "Permakleer 100" are products of the Onyx Chemical Company, N.J. and "Nimlesterol D" is a product of Emery Industries, Cincinnati, Ohio.

EXAMPLE 3

| Acid Hand Cream: | |
|---|---|
| Glyceryl Monostearate | 12.0 |
| "Ammonyx 4002" | 1.0 |
| White Petrolatum | 5.0 |
| Isopropyl Myristate | 5.0 |
| Corn Oil | 2.0 |
| "Nimlesterol D" | 2.0 |
| "Ammonyx SO" | 3.0 |
| "BTC 2125M" (50%) | 0.5 |
| "Natrasol 250 HHR" 3% aqueous | 10.0 |
| Distilled Water    q.s. | 100.0 |

"Ammonyx SO" is a product of the Onyx Chemical Company, Jersey City, N.J.

As disclosed in prior applications, the unusual method of making the polyquaternary ammonium compounds of this invention is to cause a condensation reaction to occur between approximately equimolar quantities of 1,3-bis-dimethylamino-2-propanol and 1,3-dihalo-2-propanol. This leads to a polymeric product in which most of the polymeric molecules have one halogen terminus and one dimethylamino terminus.

The same process carried out in about 10% or more excess of 1,3-dihalo-2-propanol (and then steam distilling the unreacted 1,3-dihalo-2-propanol out of the reaction mixture after the reaction) will produce a product in which almost all of the polymeric molecules have two halogen termini. And if the process is carried out in about 10% or more excess of 1,3-bis-dimethylamino-2-propanol (and then steam distilling the unreacted 1,3-bis-dimethylamino-2-propanol out of the reaction mixture after the reaction is completed) the product will be polymeric molecules almost all of which have two dimethylamino termini.

Each of these three products (i.e. one whose molecules were almost entirely terminated by halogen, one whose molecules were almost entirely terminated by dimethylamino groups, and one whose molecules were terminated by a halogen at one end of the chain, and a dimethylamino group of the other end) were tested for skin care properties.

Each of these three cosmetic formulations were tested by itself and also with each of three compounds embodying the present invention. Each of these compounds conformed to Formula (3), in one both Z's being chlorine, in the second both Z's being dimethyl amine and in the third one Z being chlorine and the other being dimethyl amine. In each of these compounds the value of n was in the range of about 2 to 30.

Those formulations containing the additive of this invention were tested at two concentrations of the additive, namely at about 0.3% and about 1.0% by weight. Since each of the polyquaternary products was prepared as a 30% aqueous solution, the approximately 0.3% concentration was prepared by adding 1 gram of a 30% polyquaternary solution to 100 grams of each stock cosmetic vehicle and thoroughly dispersing it, while the approximately 1.0% concentration was prepared by adding 3.5 grams of the 30% polyquaternary solution to 100 grams of each stock cosmetic vehicle, and dispersing it thoroughly.

Each of the products was tested in each cosmetic vehicle at both concentrations. There was no discernable difference in properties between the three products.

At both concentrations, namely at 0.3% and at 1.0% by weight, the "feel" of the skin was much softer and smoother after application of the formulations containing the additive than after application of the formulations without the additive. Furthermore, the "feel" was somewhat softer and smoother when 1.0% of the additive was used than when only 0.3% was used. However, both concentrations significantly improved the "feel".

In addition to the discovery that the uncapped polyquaternary ammonium compounds described above are excellent skin care additives, it has been discovered that certain other uncapped polymeric quaternary ammonium compounds of the same chemical structure embodied in Formula(1) are also excellent skin care additives. Exemplifying such other compounds are those disclosed in U.S. Pat. No. 3,874,870 dated Apr. 1, 1975. These compounds have the formula:

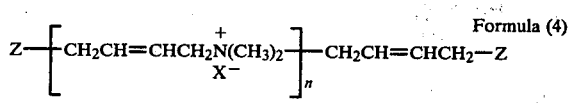

Formula (4)

wherein Z, X and n have the same definition as in Formula 3 above.

In order to illustrate the particular softening effect of the latter type of compounds, a compound made in accordance with Example 1 of U.S. Pat. No. 3,874,870 was subjected to the same test procedures as were the aforementioned compounds of Formula 3 in that the same formulations as shown in Examples, 1, 2 and 3 above were compared by themselves with the same formulations containing the same concentrations of about 0.3 percent by weight and about 1.0% by weight respectively. At both concentrations the "feel" of the skin after application was much softer in the cases when the formulation contained even 0.3% of the additive than where the formulation did not contain any, although those formulation having about 1.0 percent gave a softer "feel" than did those having only about 0.3 percent.

The same results were obtained when the compounds of formula (4) had molecules with two halogen termini, or two dimethylamino termini.

The testing of all the additives disclosed herein, as represented both by Formula(3) and by Formula(4) was done at the concentrations in the range of between about 0.3 to 1.0% by weight because this range is the most practical in use and is the preferable range, although higher or lower amounts are not necessarily excluded.

The invention claimed is:

1. A method of skin care which comprises applying to the skin a softener composition containing, as an additive, from about 0.3 to about 1.0% by weight of an uncapped linear polyquaternary ammonium compound having the formula:

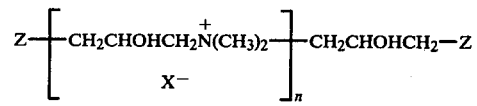

wherein Z is either X or N(CH₃)₂, X is a halogen of atomic weight above 30 and n is an integer of from 2 to about 30.

2. A cosmetic composition comprising a skin softener carrier in which is dispersed from about 0.3 to about 1.0% by weight of an uncapped linear polyquaternary ammonium compound having the formula:

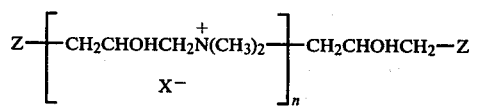

wherein Z is either X or N(CH₃)₂, X is a halogen of atomic weight above 30 and n is an integer of from 2 to about 30.

* * * * *